United States Patent
Hütter et al.

(10) Patent No.: US 7,473,029 B2
(45) Date of Patent: Jan. 6, 2009

(54) THERMOANALYTICAL SENSOR, AND METHOD OF PRODUCING THE THERMOANALYTICAL SENSOR

(75) Inventors: Thomas Hütter, Niederrohrdorf (CH); Bernd Danhamer, Niederweningen (CH); Urs Niedermann, Bubikon (CH)

(73) Assignee: Mettler-Toledo AG, Greifensee (CH)

( * ) Notice: Subject to any disclaimer, the term of this patent is extended or adjusted under 35 U.S.C. 154(b) by 0 days.

(21) Appl. No.: 11/812,728

(22) Filed: Jun. 21, 2007

(65) Prior Publication Data

US 2007/0253462 A1    Nov. 1, 2007

Related U.S. Application Data

(62) Division of application No. 10/973,900, filed on Oct. 27, 2004, now Pat. No. 7,258,482.

(30) Foreign Application Priority Data

Oct. 28, 2003  (EP) ................... 03103996

(51) Int. Cl.
*G01N 25/00* (2006.01)
*G01K 7/00* (2006.01)
*G01K 17/00* (2006.01)
*H01L 35/00* (2006.01)

(52) U.S. Cl. .................. 374/13; 374/31; 374/179; 136/225

(58) Field of Classification Search .............. 374/10, 374/13, 12, 179, 31; 136/225
See application file for complete search history.

(56) References Cited

U.S. PATENT DOCUMENTS

| 3,607,445 | A | * | 9/1971 | Hines ................. 136/225 |
| 4,110,124 | A |   | 8/1978 | Robertson et al. |
| 4,456,919 | A |   | 6/1984 | Tomita et al. |
| 5,033,866 | A |   | 7/1991 | Kehl et al. |
| 5,288,147 | A |   | 2/1994 | Schaefer et al. |
| 5,695,283 | A |   | 12/1997 | Johnson |
| 6,318,890 | B1 |  | 11/2001 | Hutter et al. |
| 6,508,585 | B2 |  | 1/2003 | Nakamura et al. |
| 6,583,391 | B2 |  | 6/2003 | Jorimann et al. |
| 6,935,776 | B2 |  | 8/2005 | Hutter |
| 2005/0076943 | A1 | * | 4/2005 | Cooper et al. ......... 136/224 |

FOREIGN PATENT DOCUMENTS

| DE | 39 16311 A1 | 10/1990 |
| EP | 0 990 893 A1 | 4/2000 |
| EP | 1 132 733 A1 | 9/2001 |
| GB | 1 357 217 A | 6/1974 |

* cited by examiner

*Primary Examiner*—Gail Verbitsky
*Assistant Examiner*—Mirellys Jagan
(74) *Attorney, Agent, or Firm*—Buchanan Ingersoll & Rooney PC

(57) ABSTRACT

In a thermoanalytical sensor with a substrate and a thermocouple arrangement that is formed at a measurement position on the substrate, an increase in sensitivity can be achieved by way of a special geometry of the thermocouple arrangement and/or the selection of the material for the substrate. In addition, a manufacturing method is proposed for the inventive sensor.

10 Claims, 5 Drawing Sheets

THERMOANALYTICAL SENSOR, AND METHOD OF PRODUCING THE THERMOANALYTICAL SENSOR

CROSS REFERENCE TO RELATED APPLICATIONS

This application claims priority under 35 U.S.C. §119 to European Application No. 03103996.9 filed in Europe on 28 Oct. 2003, the entire contents of which are hereby incorporated by reference in their entirety. This application is a DIV of 10/973,900 filed Oct. 27, 2004, now U.S. Pat. No. 7,258,482.

BACKGROUND

The invention relates to a thermoanalytical sensor with a substrate that can carry a heat flow between a heat source thermally coupled to the substrate and at least one measurement position formed on the sensor, and further with a thermocouple arrangement formed on a substantially planar surface of the substrate to deliver a thermoelectric signal. Also included in the scope of the invention is a method of producing a sensor of this kind.

Thermoanalytical sensors of this kind are used to measure physical and/or chemical properties of a substance, a substance mixture, and/or a mixture undergoing a reaction, where the measurements are performed as a function of temperature or time and where the sample that is being measured is subjected to a controlled temperature program. Other known examples are the differential heat flow calorimetry and the differential power compensation calorimetry. In both of these applications, the analysis of a sample is performed in relation to a reference sample. The sensors being used in these cases therefore have two measurement positions, i.e., one position to perform the measurements on the sample and the other position to perform the measurements on the reference sample. In the first of the aforesaid applications, the thermoelectric signal delivered by the thermocouple arrangement represents a measure for the difference between the heat flow to the sample and the heat flow to the reference sample. In the second-named application, the thermoelectric signal delivered by the thermocouple arrangement is used to control the respective heat flow rates to the sample and the reference sample in such a manner that the temperature difference between the sample and the reference sample is regulated to zero.

The thermoanalytical sensors can be configured to have the highest possible degree of sensitivity covering, if possible, the entire temperature range of the analysis, i.e., a thermoelectric signal produced as a function of the heat flow is as strong as possible in terms of signal voltage. This can help to obtain a good signal-to-noise ratio. Therefore, as a way to satisfy this, state-of-the-art thermoanalytical sensors (DE 39 16 311 C2 and EP 0 990 893 A1) have a series of thermocouple junctions of the thermocouple arrangement joined in a circuit in such a manner that the thermoelectric signal is produced as the sum of the individual thermocouple voltages. The thermocouple junctions that form the thermocouple arrangement are laid out in a circular pattern around the center of the measurement position (or around the centers of the measurement positions, if there is more than one measurement position) spaced as closely as possible to each other in the azimuthal direction. Consequently, there is no space available that would allow a further increase in the number of thermocouple junctions in these state-of-the-art arrangements.

SUMMARY

Exemplary embodiments can solve the problem of achieving a further increase in sensitivity in a thermoanalytical sensor.

Under a first exemplary aspect of the invention, a solution is proposed for a thermoanalytical sensor with a substrate that can carry a heat flow between a heat source thermally coupled to the substrate and at least one measurement position formed on the sensor, and further with a thermocouple arrangement formed on a substantially planar surface of the substrate to deliver a thermoelectric signal, wherein the thermocouple arrangement includes a chain of thermocouple junctions which are composed of two different thermocouple materials and serially connected to form a thermocouple column. The chain of thermocouple junctions reaches in the azimuthal direction around the center of the measurement position, with the individual thermocouple junctions arranged at alternatingly different radial distances from the center of the measurement position. According to an exemplary embodiment, at least one of the interstitial surface portions that are azimuthally confined between a first thermocouple junction closest to the center and the two immediately neighboring second thermocouple junctions in the chain contains a third thermocouple junction and a fourth thermocouple junction that are direct neighbors to each other in the chain.

In the thermocouple column that is formed by this serially connected chain of thermocouple junctions, any two thermocouple junctions that are direct neighbors in the chain have a radial distance from each other. Thus, when there is a heat flow either in the direction towards the center of the measurement position or away from the center of the measurement position, a temperature difference will occur between any two neighboring thermocouple junctions in the chain because of the thermal resistance of the sensor. The temperature difference, in turn, will give rise to thermo-voltages between neighboring thermocouple junctions in the chain which, because of the serial chain arrangement, are added up as a voltage sum. Thus, the resultant overall thermoelectric signal represents the sum of the respective individual thermo-voltages that occur in each of the pairs of directly neighboring first and second thermocouple junctions as well as in the pairs of directly neighboring third and fourth thermocouple junctions. The pairs of thermocouple materials can be the same for all of the thermocouple junctions. One can also use a plurality of different pairs of thermocouple materials to form the thermocouples instead of only one pair of different materials. As each of the pairs of directly neighboring third and fourth thermocouple junctions is arranged in the free interstitial space confined azimuthally between one of the first thermocouple junctions and the two immediately neighboring second thermocouple junctions, the space available on the sensor surface is optimally utilized to increase the total number of thermocouple junctions. In this arrangement, the third thermocouple junctions can be arranged at a relatively close radial distance to the first thermocouple junctions, the latter being located at the shortest radial distance from the center of the measurement position, while the fourth thermocouple junctions can be arranged at a relatively close radial distance to the second thermocouple junctions. A crucible that serves to hold an analysis sample can be dimensioned so that in the measurement position, the bottom surface of the crucible covers the first and third thermocouple junctions, while the second and fourth thermocouple junctions remain uncovered since they lie on a larger radius from the center of the measurement position. With a crucible designed in this manner, the thermocouple arrangement can be particularly effective in measuring a radial temperature gradient that occurs in the vicinity of the crucible and corresponds to the heat flow exchanged between the heat source and the crucible.

A particularly advantageous embodiment of the invention can use a configuration where the first thermocouple junctions lie on a first circle whose midpoint is located at the center of the measurement position; the second thermocouple junctions lie on a second circle concentric to and with a larger radius than the first circle; the third thermocouple junctions lie on a third circle concentric to the first circle and with a radius that is larger than the radius of the first circle but smaller than the radius of the second circle; and the fourth thermocouple junctions lie on a fourth circle concentric to the first circle with a larger radius than the third circle. This arrangement conforms to the provision of radial symmetry of the measurement position or positions (if the arrangement has more than one measurement position) relative to the center, and it also conforms to the customary radially symmetric shape of the sample crucibles that is compatible with the symmetry requirement. The circular bottom surfaces of the crucibles designed for use with this embodiment of the thermoanalytical sensor are dimensioned with a radius that is larger than the radius of the third circle but smaller than the radius of the second circle.

To come as close as possible to a perfect radial symmetry, it is further helpful that the thermocouples are arranged on their respective circles at equal angular intervals. To make the radial symmetry as complete as possible, it is likewise helpful that the thermocouple material between neighboring first and second thermocouple junctions in the chain extends in the shape of rectilinear strip sections and that the thermocouple material between third and fourth thermocouple junctions that are immediate neighbors in the chain and lie within the same interstitial area likewise extends in the shape of rectilinear strip sections. The overall thermocouple arrangement in these cases has the appearance of a doubled-up star, i.e., two individual stars nested in each other and centered on the midpoint of the measurement position. With this design, the surface area is used very efficiently, allowing the arrangement of a particularly large number of thermocouple junctions and a commensurately high sensitivity of the sensor. As a further advantage, this arrangement is expandable by adding further nested stars as long as the inside circle of thermocouple junctions of the outermost star has a smaller radius than the outside circle of thermocouple junctions of the innermost star.

It further serves the purpose of achieving radial symmetry that the thermocouple material connecting each third thermocouple junction to that of its neighboring fourth junctions which lies in the next interstice of the star contains an azimuthally directed track portion. This azimuthal track portion can take the shape of a segment of a circle whose radius (from the midpoint of the measurement position) is slightly larger than the circle radius of the second thermocouple junctions that separate the interstices of the star from each other. In this arrangement, one end of the azimuthal portion can meet the end of a track portion consisting of the other of the two thermocouple materials to form the fourth thermocouple junction, while the other end of the azimuthal portion can continue into a radial portion extending to the third thermocouple junction in the neighboring interstice.

To connect the thermoanalytical sensors to a processing circuit, it is of practical advantage that connector terminals are formed on the surface of the substrate. These terminals are connected to the ends of the thermocouple column and serve to tap the thermoelectric sensor signal. They can be configured in the shape of flat connector pads or connector spots where connecting wires to a processing circuit can be attached.

In particular, it is envisaged within the scope of the invention that more than one of the measurement positions are arranged on the sensor. Specifically, one of the measurement positions can serve as reference position, while the other measurement positions serve to receive test samples. The reference position can either remain empty, or it can be occupied by an inert reference sample of known properties. If a differential calorimetry experiment is to be performed, the respective thermoelectric signals from the individual measurement positions can be combined through an appropriate circuit arrangement in such a manner that the respective differential signals between the reference position and each of the sample positions can be obtained directly.

An exemplary embodiment of the inventive sensor has two measurement positions arranged on one sensor unit. In this arrangement, one of the measurement positions can be used as reference position and the other as sample position. This configuration is analogous to arrangements used for differential heat flow calorimetry which will be familiar to those engaged in this field.

In an advantageous alternative embodiment of the invention, it is envisaged to arrange four of the measurement positions on one sensor unit in a configuration where a straight line between the centers of one pair of the positions perpendicularly bisects a straight line between the centers of the other pair, and vice versa. Thus, the centers of the four measurement positions lie at the corners of an imaginary square. This arrangement is advantageous in that it optimizes the thermal symmetry of all of the measurement positions.

The thermocouple arrangements in the sensors discussed up to this point serve to sense a heat flow between the measurement position and the heat source, or to sense a difference between heat flows associated with different measurement positions. In addition, in thermoanalytical applications it is considered advantageous to provide embodiments of the invention where a further thermocouple arrangement is formed at the measurement position on the surface of the substrate for the purpose of delivering a thermoelectric signal representing the absolute temperature at the measurement position, with separate connector terminals to tap the signal representing the absolute temperature. It is a known fact that thermocouples can only provide a direct measurement of temperature differences. If an absolute measurement is to be performed, the temperature at one of the measurement positions has to be known or held constant. According to the state of the art, the exposure of one of the measurement positions to the known temperature occurs outside of the sensor. The information that is thereby gained regarding the absolute temperature of a measurement position can be used for example to perform a mathematical correction of deviations from thermal symmetry in sensors with a plurality of measurement positions in cases where such deviations escape detection by a mere differential temperature measurement between the measurement positions and where the failure to detect the deviation would cause an error in the result of the analysis, because as a consequence of the asymmetry, the temperature difference does not precisely correlate to the difference between the heat flows at the different measurement positions.

In a practical design configuration, the thermocouple arrangement that serves to supply the thermoelectric signal representing the absolute temperature has an area containing a first thermocouple material that is arranged in a surface portion delimited by the thermocouple junctions which surround the measurement position, with a connector portion leading to one of the connector terminals that are arranged on the surface. In this configuration, the further thermocouple arrangement for the sensing of the absolute temperature is concentrated around the center of the measurement position and thus in direct thermal contact with the measurement position, i.e., with the sample that occupies the measurement position. As a practical measure to optimize the radial symmetry of the arrangement as much as possible, the delimited area of the first thermocouple material can, for example, be configured in the form of a circular ring.

In order to produce a thermoelectric signal representing the absolute temperature and to make it possible to tap the signal, a thermocouple junction with a second, different thermocouple material is arranged on the delimited portion of the first thermocouple material, with the second thermocouple material extending to one of the connector terminals formed on the surface.

An improvement in simplicity and a particularly efficient use of the available surface space on the sensor can be achieved through a design configuration where, for example, two of the measurement positions are formed on the sensor, with a connection between the second thermocouple materials of the two measurement positions being formed on the substrate and routed to a common terminal. The thermoelectric signals representing the absolute temperatures of the measurement positions are obtained by tapping the respective voltages between the common terminal and the two terminals that are connected to the first thermocouple material at the two measurement positions.

In a further practical embodiment which has a purpose of, for example, minimizing the pattern of connector terminals that have to be arranged on the substrate, two of the measurement positions are formed on the sensor and a connection is formed on the substrate between two electrically equivalent ends of the respective thermocouple columns associated with the measurement positions, while the other ends of the two thermocouple columns are connected to terminals that are formed on the substrate and serve to tap the difference between the respective thermoelectric signals of the two thermocouple columns. In this configuration, the two thermocouple columns are connected so that they oppose each other electrically, with the result that the thermoelectric signal occurring at the two terminals represents a difference of the temperatures at the two measurement positions.

For the evaluation of the results and the calculation of corrections, it can further be desirable to provide a possibility for tapping the respective output signals of the two thermocouple columns separately. Again in the interest of minimizing the structure of connector terminals required on the substrate, it is advantageous if the aforementioned connection between the two electrically equivalent ends of the thermocouple columns is also connected to a common terminal formed on the substrate. Thus, the respective output signal of each thermocouple column can be tapped separately between the common terminal and the terminal at the other end of the respective thermocouple column.

Within the scope of the invention, it is envisaged in particular that the thermocouple arrangements formed on the substrate are configured as thick film arrangements. The concept of using thick film technology to produce the thermocouple arrangements on the substrate is presented in the above-referenced German patent DE 39 16 311 C2 and the underlying German patent application publication DE 39 16 311 A1 with a discussion of the advantages that are achieved by using thick film technology. The disclosure of these two documents is hereby included by reference in the present disclosure. In particular, using thick film technology provides a simple solution to the problem of insulating the individual structural elements of the thermocouple arrangements against the outside, i.e., against sample crucibles or reference sample crucibles that are placed on the measurement positions.

To achieve the desired thermally inert behavior and durability of the sensor, it is advantageous if the substrate consists of or contains, a ceramic material.

Under a second exemplary aspect of the invention, a further solution is proposed for a thermoanalytical sensor with a substrate that can carry a heat flow between a heat source thermally coupled to the substrate and at least one measurement position formed on the sensor, and further with a thermocouple arrangement formed on a substantially planar surface of the substrate to deliver a thermoelectric signal, wherein the thermocouple arrangement includes a chain of serially connected thermocouple junctions which are composed of two different thermocouple materials. According to an exemplary embodiment, the thermocouple junctions are arranged in two or more planes that lie on top of each other, with each plane being insulated from the next plane by an insulating layer, each plane containing a section of the circuit arrangement, and each section being formed by conductor leads connecting the thermocouple junctions, where the overall circuit arrangement is formed by connecting the appropriate ends of the sections to each other by interlayer contacts.

According to the embodiment just outlined, the overall circuit arrangement is subdivided into at least two sections. As the thermocouple junctions that belong to the individual sections are arranged on top of each other, the available surface area on the sensor is multiplied in accordance with the number of planes that are layered on top of each other. Consequently, the circuit arrangement can contain a corresponding multiple of the number of thermocouple junctions. The result is a commensurate increase in the strength of the thermoelectric signal delivered by the circuit arrangement and in the sensitivity of the sensor.

As an advantageous way of realizing the foregoing features, terminals for tapping the thermoelectric signal of the thermocouple arrangement are formed in the top plane relative to the substrate, and one end of the circuit section that occupies the bottom plane is connected to one of the terminals through interlayer contact. The ability to tap the thermoelectric signal from the terminals lying in the top plane facilitates the installation and connection of the sensor in a thermoanalytical instrument.

In an advantageous embodiment, the thermocouple junctions within a section of the circuit arrangement are connected in series and the sections, in turn, are serially connected to form the circuit arrangement, so that the result is a thermocouple column.

With preference, the thermocouple junctions are arranged so that they proceed in the azimuthal direction around the center of the measurement position and lie at alternatingly different radial distances from the center.

In a further advantageous configuration, the sections of the circuit arrangement that lie in different planes are of a substantially congruent shape.

Under a third exemplary aspect of the invention, a further exemplary embodiment is proposed to provide in a thermoanalytical sensor with a substrate that can carry a heat flow between a heat source thermally coupled to the substrate and at least one measurement position formed on the sensor, and further with a thermocouple arrangement formed on a substantially planar surface of the substrate to deliver a thermoelectric signal, wherein the thermocouple arrangement includes a serial chain of thermocouple junctions associated with the measurement position, the junctions being composed of two different thermocouple materials and connected into a circuit arrangement, and wherein the substrate has a thermal conductivity that does not exceed 5 Watt per meter and per degree Kelvin.

A thermal conductivity of this reduced magnitude in comparison to the conventional aluminum oxide substrates has the effect that a stronger temperature gradient develops between the thermocouple junctions that are exposed to the different temperature levels. As a result, the thermoelectric signal produced by the thermocouple arrangement is commensurately increased and, consequently, the sensitivity and signal-to-noise ratio of the sensor are improved. However, as a cautionary remark, as the thermal conductivity of the substrate is decreased, the time constant of the sensor is increased. Even under the hypothetical assumption that materials technology imposes no limits on lowering the thermal conductivity, in an exemplary embodiment, a bottom limit that should not be traversed is represented by a level of thermal conductivity where the time constant of the substrate is still marginally adequate.

In this regard, the range of interest for practical applications includes materials with a thermal conductivity no lower than 0.5 W/(m×K).

Using a low thermal conductivity, a conductivity value of, for example, no more than 3 W/(m×K) is preferred, with an even higher level of preference for values not exceeding 2 W/(m×K). This leads to particularly noticeable improvements in comparison to conventional aluminum oxide substrates.

In a practical embodiment, a special ceramic material is selected for the substrate, with a lower conductivity value than the conventional ceramic oxide materials, but with favorable mechanical and electrical properties comparable to the oxide ceramics. To name an example, the substrate material that is available under the trade name PYTHAGORAS has been found suitable, having a thermal conductivity around 2 W/(m×K). Also suitable, albeit less desirable in regard to its mechanical properties, the glass ceramic substrate which is available under the product name MACOR has a thermal conductivity of significantly less than 2 W/(m×K).

A fourth exemplary aspect of the invention relates to a method of producing a thermoanalytical sensor wherein a design pattern of at least two different thermocouple material pastes is printed by way of a thick-film technique onto a substantially planar surface of a substrate. The thick-film pattern, which is fired after printing, represents a thermocouple arrangement with a serially connected chain of thermocouple junctions composed of two different thermocouple materials and associated with at least one measurement position, which serves to deliver a thermoelectric signal. An exemplary method is distinguished by the fact that the circuit pattern is divided into at least two partial patterns, that a first partial pattern is produced in thick-film technology on the substrate, an insulating layer with contact passage holes for the connection of the partial patterns is overlaid on the first partial pattern, a further partial pattern is produced on the insulating layer, and the foregoing procedure is repeated until all partial patterns are produced above one another.

By using thick-film technology, the structure of the partial patterns and insulating layers can be produced on the substrate at a relatively low cost. Conventional pastes can be used for the thermocouple materials, for example gold paste for one of the thermocouple materials and gold/palladium paste for the other thermocouple material. If desired, it is possible to use other materials in order to produce thermocouples with different properties. The pastes can be applied by a known procedure using screen-printing techniques in accordance with the prescribed patterns. Each application of a pattern is followed by a firing operation. In particular, one can first apply and fire one of the thermocouple materials for each partial pattern and subsequently apply and fire the other thermocouple material in accordance with the respective partial pattern. Performing the two firing operations separately has a favorable effect on the thermoelectric conductivity of the thermocouples that are formed in the manner just described.

In advantageous embodiments of the inventive method, the partial patterns are configured in such a way that the repetitive procedure of applying each partial pattern as a layer directly produces the thermoanalytical sensors with the preferred circuit configurations. In a first embodiment of this kind, the partial patterns are designed substantially congruent to each other. In a further embodiment, each partial pattern is serially connected to the next by only one connection, whereby the number of interlayer connections can be kept small. In a further embodiment, the topmost partial pattern relative to the substrate is overlaid with an insulating layer with connector terminals from which the thermoelectric signal can be tapped, wherein at least one of the connector terminals is joined through interlayer contact to the partial pattern in the bottom layer relative to the substrate.

BRIEF DESCRIPTION OF THE DRAWINGS

In the description that follows below, exemplary embodiments of the invention are explained in more detail with references to the drawings, wherein.

DETAILED DESCRIPTION

Figure 1:
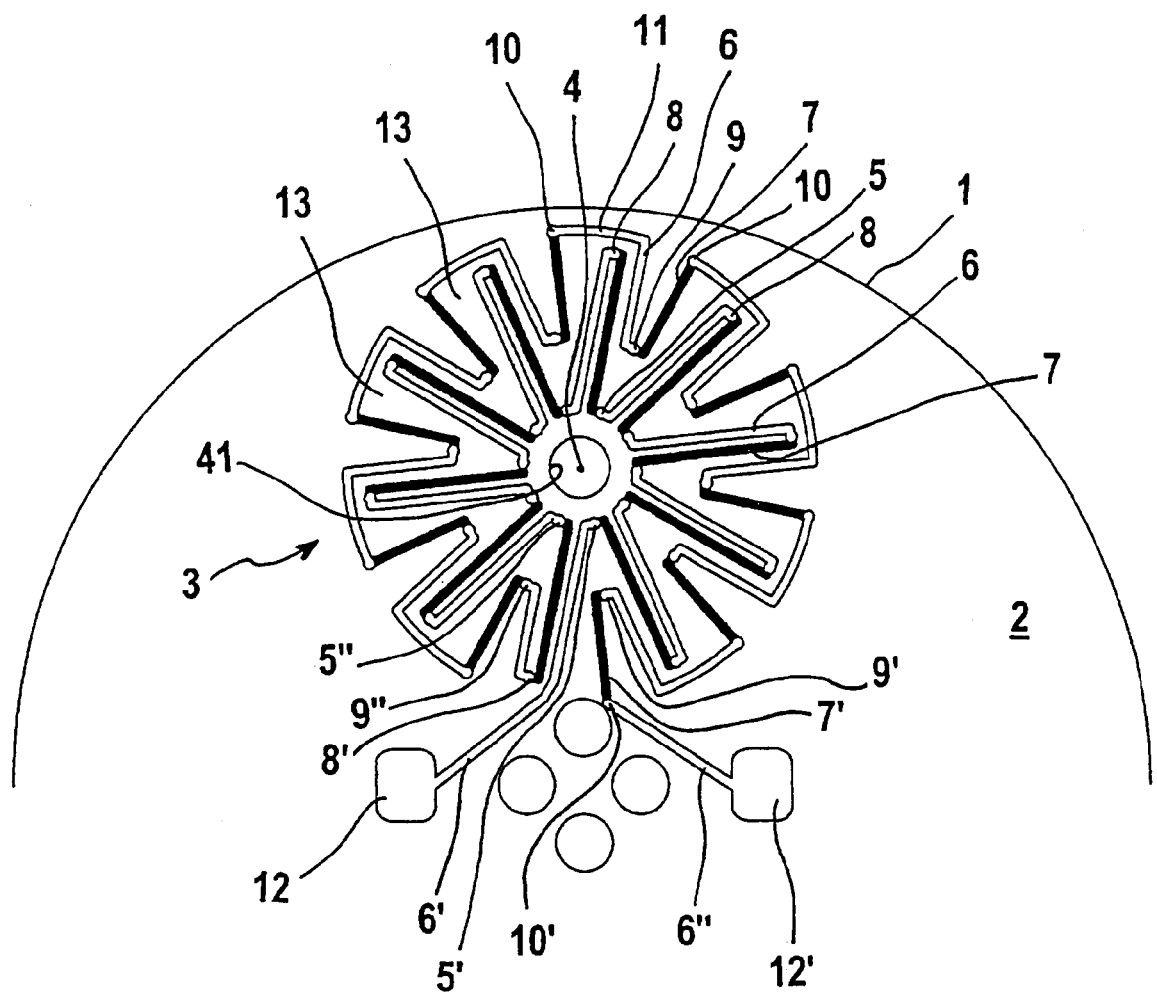
FIG. 1 schematically represents a plan view of a thermoanalytical sensor according to a first exemplary embodiment of the invention arranged in the area of a measurement position.

A thermoanalytical sensor according to a first exemplary embodiment of the invention has a cylindrical substrate 1, where the height of the cylinder is small in relation to its radius. FIG. 1 represents in schematic form a plan view of a top surface 2 of the substrate which has the shape of a circular disk, as seen in the direction of the cylinder axis of the substrate 1. In the area delimited between the cylinder axis and the radially outer border of the surface 2, a measurement position 3 is arranged which is equipped with a thermocouple arrangement that has been put in place through a thick-film technology procedure.

In this thermocouple arrangement, strip-shaped sections of two different thermocouple materials overlap at each of their adjoining ends, so that a series of thermocouple junctions is formed by these overlaps. The thermocouple junctions are arranged on four concentric circles whose common center point 4 represents the center of the measurement position 3.

The first thermocouple junctions, which are located on the first circle closest to the center are identified in FIG. 1 by the reference symbol 5. Each of the first thermocouple junctions is composed of overlapping, short azimuthal end portions of the two different thermocouple materials 6 and 7. From the azimuthal end portions, the thermocouple materials 6 and 7 extend narrowly spaced from each other and parallel to each other in a substantially outward radial direction relative to the center 4 to a second circle, where the second thermocouple junctions 8 are formed likewise by overlapping, short azimuthal end portions analogous to the first thermocouple junctions 5.

The third thermocouple junctions 9 lie on the third circle, whose radius is larger than the radius of the first circle and smaller than the radius of the second circle. Similar to the first thermocouple junctions 5, the third thermocouple junctions 9 have short azimuthal overlapping end portions of the two thermocouple materials 6 and 7. From the third thermocouple junctions 9, the thermocouple materials 6 and 7 extend substantially in the shape of strip sections in an outward radial direction to the fourth circle, whose radius is larger than the radius of the second circle. The ends of the strips of the thermocouple material 7 lie on the fourth circle where they meet and overlap with the ends of the thermocouple material 6 to form the fourth thermocouple junctions 10. From the fourth thermocouple junctions 10, the thermocouple material 6 extends in the azimuthal direction following the fourth circle. Each of the azimuthal strip sections 11 of the first thermocouple material 6 extends from a fourth thermocouple junction 10 to the substantially radial strip section of the thermocouple material 6 that originates from the azimuthally nearest neighboring third thermocouple junction 9. The first, second, third and fourth thermocouple junctions 5, 8, 9, and 10, respectively, are arranged on their respective circles at equal azimuth-angle intervals from each other.

Deviating from a completely symmetric configuration of the first thermocouple junctions 5, one first thermocouple junction 5' is distinguished by the fact that the substantially radial strip section of the first thermocouple material 6' which originates from the junction 5' continues beyond the radius of the second circle to a terminal pad 12 that is formed on the surface 2 of the substrate 1. This first thermocouple junction 5' forms the end of a thermocouple column in which all thermocouple junctions 5, 5', 8; 9 and 10 are connected in a serial sequence. The other end of the thermocouple column is formed by the fourth thermocouple junction 10' serially following the third thermocouple junction 9' that lies radially next to the aforementioned first thermocouple junction 5'. The strip section of thermocouple material 7' which runs from the third thermocouple junction 9' in a substantially outward radial direction is at its outer end on the fourth circle joined to a strip section of the thermocouple material 6" to form the fourth thermocouple junction 10'. The strip section of the thermocouple material 6" runs to a terminal pad 12' that is formed on the surface 2.

The drawing and the accompanying description given in the foregoing paragraphs also make it clear that the thermocouple materials 6, 7, 7' are, in an exemplary embodiment, overlaid on each other only in the areas where they mutually overlap and thereby, i.e., through the contact provided by the overlap, form the thermocouple junctions 5, 5', 8, 9, 10, 10'. All other parts of the thermocouple materials 6, 7, 7' run side-by-side in one and the same plane.

In the serially connected sequence that forms the thermocouple column beginning at the first thermocouple junction 5', each first thermocouple junction 5 or 5' has a second thermocouple junction 8 as its immediate neighbor until the counterclockwise azimuthal loop about the center point 4 has reached the first thermocouple junction 5" which, in the azimuthal direction, lies next to the starting thermocouple junction 5' of the column. The junction 5" is connected through the substantially radially directed strip section of the thermocouple material 7 to a further thermocouple junction 8' which has a third thermocouple junction 9" as its immediate neighbor in the serial sequence, followed by pairs of immediately neighboring fourth and third thermocouple junctions 10 and 9, respectively, until the fourth thermocouple junction 10' has been reached which forms the other end of the thermocouple column. The overall thermocouple arrangement has the appearance of a doubled-up star. The thermocouple materials 6, 7 that extend in the shape of rectilinear strips between the first and second thermocouple junctions 5 and 8 form an inner star and delimit between each other azimuthal interstitial areas 13. In each of the interstitial areas 13 lies a pair 9, 10 of third and fourth thermocouple junctions that are immediate neighbors in the serial sequence. The third and fourth thermocouple junctions 9, 10 with their connecting strip sections of thermocouple materials 6, 7 form the outer star. The arrangement could be continued in analogous manner with a further azimuthal ambit in counterclockwise direction starting at the thermocouple junction 10'.

Figure 2:
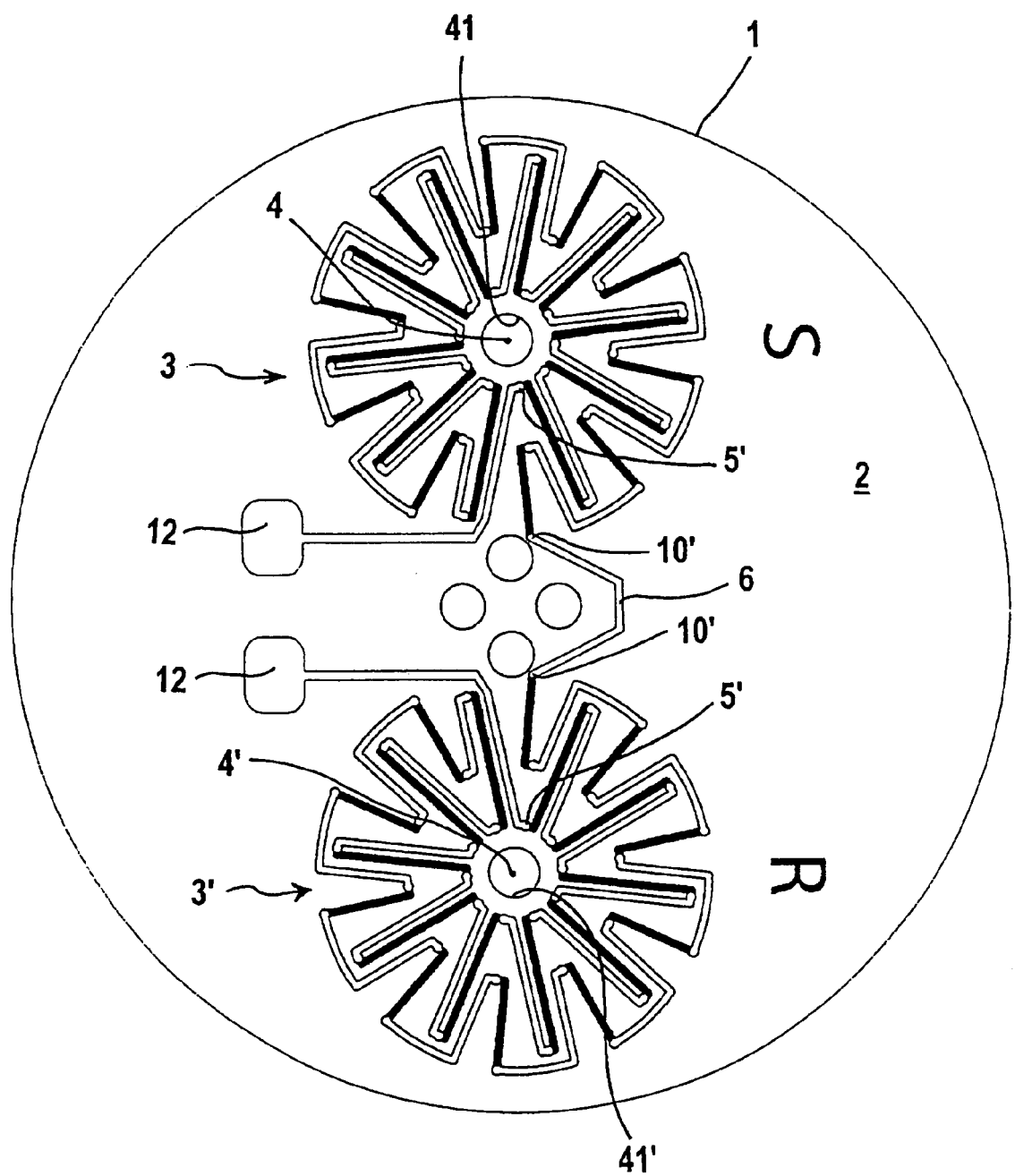
FIG. 2 schematically represents a plan view of a thermoanalytical sensor according to a second exemplary embodiment of the invention with two measurement positions.

A thermoelectric sensor according to a second exemplary embodiment of the invention is shown in FIG. 2, using an analogous form of representation as in FIG. 1. In this embodiment there are two measurement positions 3, 3', each with a structure that is completely equivalent to the measurement position 3 as described above in the context of FIG. 1. The reader is therefore referred to the description of FIG. 1 for the structural details of the second embodiment. The two measurement positions 3 and 3' of the second embodiment are arranged at equal distances diametrically opposite to each other relative to the cylinder axis of the substrate 1. The letter "S" for "Sample" is printed on the substrate surface 2 near the measurement position 3, and the letter "R" for "Reference" is printed near the measurement position 3'. This indicates that a sample is to be placed on the measurement position 3, and an inert reference sample is to be placed on the measurement position 3'.

The arrangement in FIG. 2 deviates from FIG. 1 only in that the fourth thermocouple junction 10' at the end of the thermocouple column formed at the measurement position 3 and likewise the fourth thermocouple junction 10' at the end of the thermocouple column formed at the measurement position 3' are not each connected to a separate terminal pad 12' in analogy to the terminal pad 12' in FIG. 1. Instead, these ends of the two thermocouple columns are joined by a strip section of the thermocouple material 6. The first thermocouple junctions 5' that form the other ends of the respective thermocouple columns at the measurement positions 3 and 3' are each connected to a terminal pad 12 in the same manner as in FIG. 1. Through this design configuration, the two thermocouple columns are arranged so that they electrically oppose each other in the circuit. Thus, by tapping the two terminal pads 12 in the second embodiment, one obtains the difference between the respective thermoelectric signals of the two thermocouple columns, while the first embodiment delivers between the terminal pads 12, 12' the entire thermoelectric signal produced by the thermocouple column that is formed on the measurement position 3.

Figure 3:
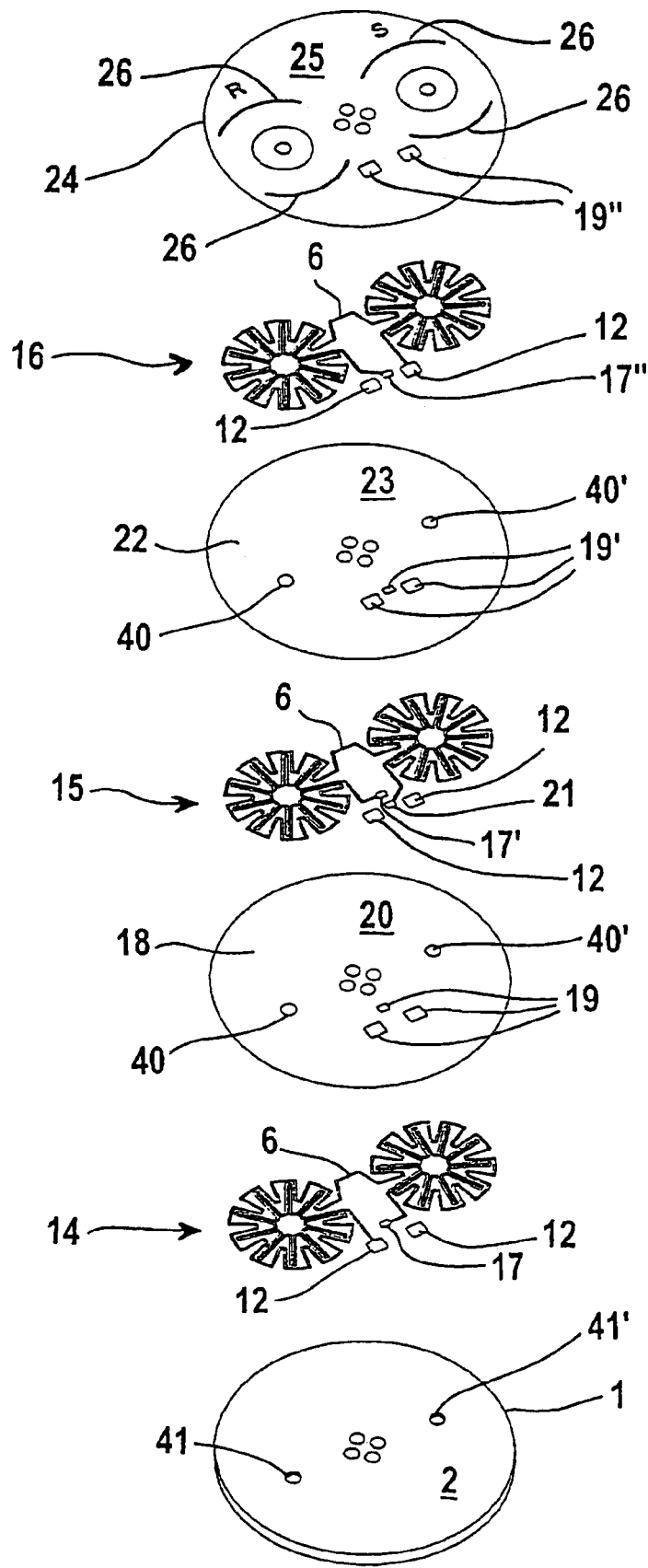
FIG. 3 represents an exploded view of a thermoanalytical sensor according to a third exemplary embodiment of the invention.

In the thermoanalytical sensor according to a third exemplary embodiment of the invention, the overall pattern formed by the thermocouple materials and thermocouple junctions of the thermocouple arrangement is subdivided into a plurality of partial patterns which are arranged on top of each other, with the appropriate electrical terminations of the partial patterns being connected to each other. This concept is illustrated in FIG. 3, shown in an exploded view for the sake of clarity, wherein the individual strata of the layered arrangement are shown pulled apart from each other in the direction of the cylinder axis of the substrate 1 which is identical to the substrates shown in FIGS. 1 and 2. The arrangement of FIG. 3 has a total of three partial patterns 14, 15 and 16, respectively, each of which is configured analogously to the pattern forming the thermocouple arrangement in the second embodiment which is represented in FIG. 2. Minor deviations from the pattern shown in FIG. 2 exist only to the extent necessary for forming the connections of the electrical terminations of the partial patterns.

In FIG. 3, the partial pattern 14 at the bottom is arranged on the surface 2 of the substrate in the same manner as in FIG. 2. Likewise as in FIG. 2, the thermocouple material from the first thermocouple junction 5' that forms one end of the overall circuit arrangement represented by the entire pattern is connected to the terminal pad 12. Also as in FIG. 2, the part of the pattern shown on the left side is joined to the right-hand part by means of the connecting strip 6 of thermocouple material. However, in contrast to FIG. 2, the analogous first thermocouple junction at the end of the right-hand part in FIG. 3 is connected to an interlayer contact pad 17 which is arranged at a distance from the left-hand terminal pad 12 in FIGS. 2 and 3 as well as from a second terminal pad 12 that corresponds to the right-hand terminal pad in FIG. 2 but is configured as an insular pad in FIG. 3, i.e., non-contiguous with the rest of the partial pattern.

The partial pattern 14 that is arranged on the surface 2 is topped by an insulating layer 18 that is equipped with interlayer contact holes 19 at matching positions for the interlayer contact pad 17 and the two terminal pads 12. On the surface 20 that faces away from the partial pattern 14, the insulating layer 18 carries the partial pattern 15. At the analogous position where the bottom-layer partial pattern 14 has an end connection to the terminal pad 12, the middle-layer partial pattern 15 has an end connection to an interlayer contact pad 17' which is connected to the interlayer contact pad 17 by way of the interlayer contact hole 19 that is congruent with the interlayer contact pads 17 and 17'. Where the bottom-layer partial pattern 14 has an end connection to the interlayer contact pad 17, the right-hand part of the partial pattern 15 in FIG. 3 has an analogous end connection to an interlayer contact pad 21 which is electrically insulated against the bottom layer by the insulating layer 18. The two terminal pads 12 of the bottom layer are brought out through the congruently positioned interlayer contact holes 19 to the surface 20 of the insulating layer 18 where they appear as insular pads.

The surface 20 of the insulating layer 18 which carries the partial pattern 15 is topped by an insulating layer 22 that is equipped with interlayer contact holes 19' at matching positions for the interlayer contact pad 21 and the two terminal pads 12. The surface 23 of the insulating layer 22 carries the partial pattern 16, which forms the topmost partial pattern in FIG. 3. The end connection of the left-hand part leads to an interlayer contact pad 17" which is connected to the congruently positioned interlayer contact pad 17' of the middle-layer partial pattern 15 by way of a likewise congruently positioned interlayer contact hole 19' of the insulating layer 22. The end connection of the right-hand part leads to the right-hand terminal pad 12 in FIG. 3, which is contacted directly through all layers by way of congruently located interlayer contact holes 19' and 19 of the insulating layers 22 and 18, respectively. The left-hand terminal pad 12 connects through analogous interlayer contact holes 19' and 19 to the left-hand terminal pad 12 of the bottom-layer partial pattern 14 in FIG. 3.

On top of the surface 23 of the insulating layer 22 that carries the topmost partial pattern 16 there is an insulating layer 24 equipped only with interlayer contact holes 19'' that match the positions of the terminal pads 12. The thermoelectric signal delivered by the entire circuit arrangement can be tapped at the terminal pads 12 that are contacted through the interlayer contact holes 19''. The signal represents the sum of the thermo-voltage differences delivered by the individual partial patterns 14, 15 and 16 between the left-hand part and the right-hand part of each partial pattern.

Furthermore, in addition to the symbols "R" and "S" mentioned already in the context of FIG. 2, the exposed surface 25 of the insulating layer 24 carries arc-shaped markings 26 to facilitate the centered positioning of the sample- and reference crucibles relative to the center points 4 and 4' of the respective measurement positions (see FIG. 2).

The third embodiment shown in FIG. 3 can be produced in particular with the use of thick-film technology. The process starts by screen-printing and firing the partial pattern 14 with suitable thermocouple material pastes on the surface 2 of the substrate 1. This operation preferably can be performed in two steps, the first of which consists of the application and immediate firing of only those structural components of the pattern that consist of a first thermocouple material. In the second step, the structural elements consisting of the other thermocouple material are printed and the firing is repeated. This two-step procedure has a favorable effect on the quality of the thermocouple junctions. After the insulating layer 18 has been put in place, the second partial pattern 15 is produced in the same manner, and the foregoing procedure is repeated until all insulating layers and partial patterns have been completed, at which point the topmost insulating layer 24 is put in place.

Figure 4:
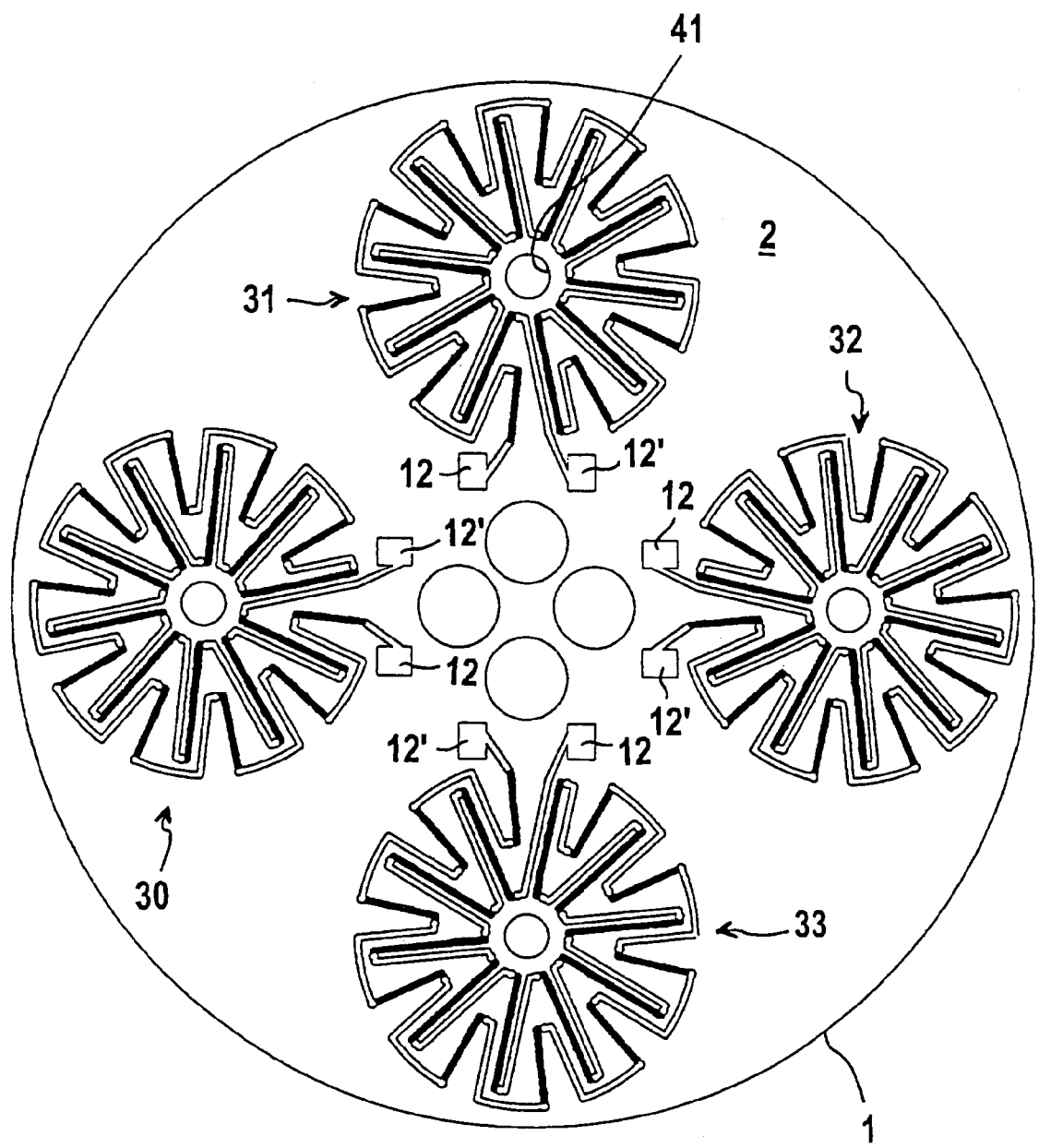
FIG. 4 schematically represents a plan view of a thermoanalytical sensor according to a fourth exemplary embodiment of the invention.

The thermoanalytical sensor according to a fourth exemplary embodiment of the invention is shown in FIG. 4 in a form of representation that is analogous to FIG. 1. This fourth embodiment has a total of four measurement positions 30, 31, 32 and 33, respectively, each of which has an analogous configuration to the measurement position 3 in FIG. 1. In regard to the individual measurement position, the reader is therefore referred to the description of the embodiment shown in FIG. 1. Particularly like in FIG. 1, the end portions of the individual thermocouple columns are connected to a pair of terminal pads 12, 12' where the thermoelectric voltage can be tapped that is produced by the respective column. The centers of the four measurement positions 30, 31, 32, 33 are located on the corners of a square whose diagonals intersect in the cylinder axis of the substrate 1.

Figure 5:
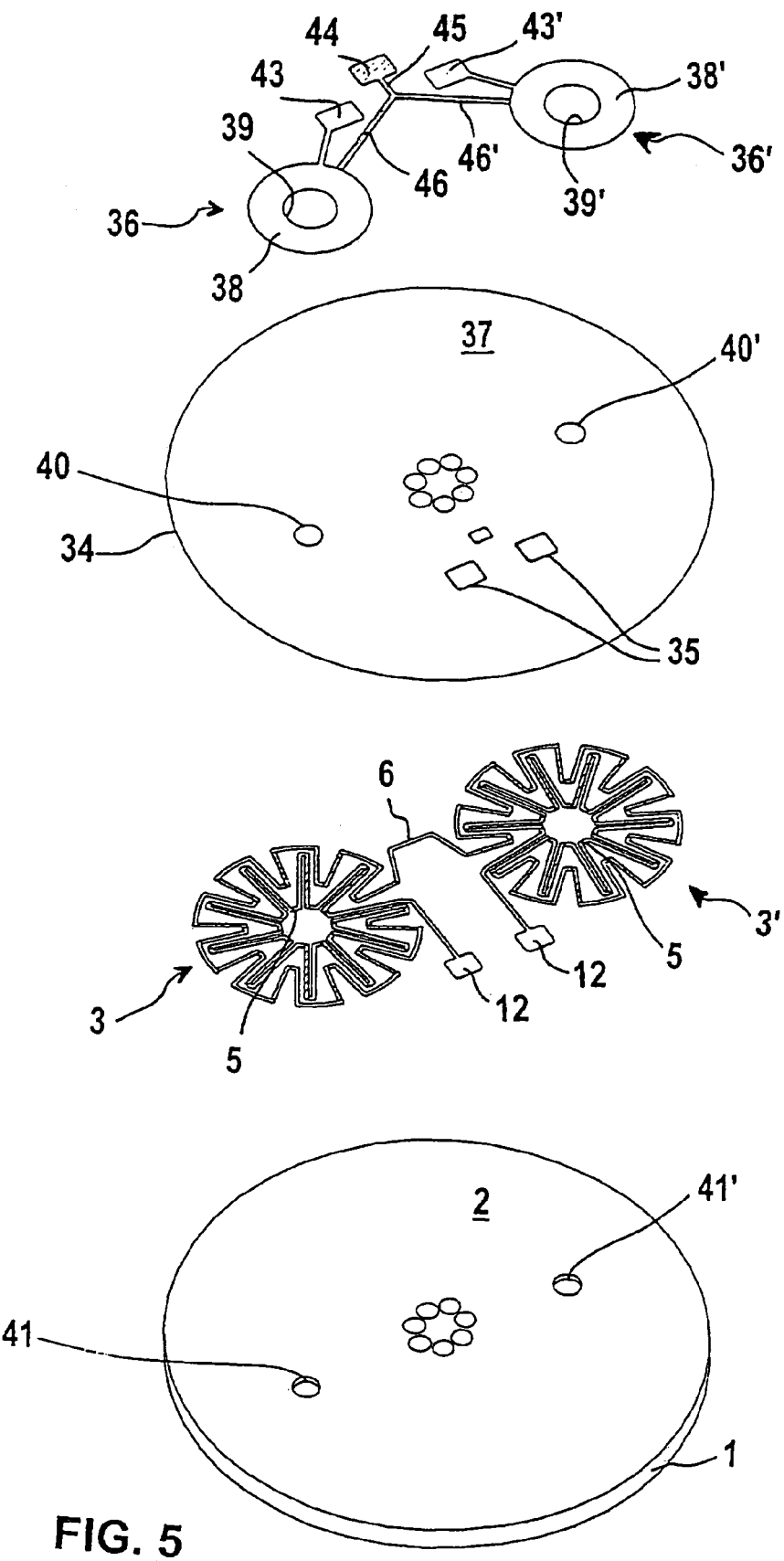
FIG. 5 represents an exploded view of a thermoanalytical sensor according to a fifth exemplary embodiment of the invention.

The thermoanalytical sensor according to a fifth embodiment of the invention is shown in FIG. 5 in an exploded view where the layers of the arrangement are pulled apart in the direction of the cylinder axis of the substrate 1. In regard to the differential circuit arrangement that is formed between the two doubled-up star patterns by means of the connector 6 and the two terminal pads 12, the fifth embodiment is completely analogous to the second embodiment which is described in the context of FIG. 2. Insofar as the differential circuit arrangement is concerned, the reader is therefore referred to the description of FIG. 2. However, FIG. 5 additionally shows an insulating layer 34 which is also present in the second embodiment but is not shown in FIG. 2. The insulating layer 34 has windows 35 matching the locations of the terminal pads 12 of the thermocouple arrangement, so that the differential thermoelectric signal can be accessed at the windows 35. The insulating layer 34 allows metallic crucibles to be placed on the measuring positions without thereby causing short circuits between the thermocouple junctions.

In addition to the features which have just been described and are already part of the second embodiment in accordance with FIG. 2, the fifth embodiment has at each of the two measurement positions 3, 3' a further thermocouple arrangement 36, 36', respectively, on the exposed surface 37 of the insulating layer 34. Each of these further thermocouple arrangements 36, 36' includes a ring-shaped first thermocouple material 38, 38' in a centered arrangement relative to the center 4, 4' of the respective measurement position 3, 3'. In FIG. 5, the two further thermocouple arrangements 36, 36' are, for the sake of clarity, drawn to a magnified scale in comparison to the lower parts of the exploded drawing. In actuality, the ring-shaped first thermocouple material 38, 38' is arranged within the respective first circle on which the first thermocouple junctions 5 are located. In the areas delimited, respectively, by the inside perimeters 39, 39' of the ring-shaped arrangements 38, 38', the insulating layer 34 and the substrate each have respective congruently located axial passage openings 40, 40' and 41, 41'. Passage openings of this kind also exist in the other, previously described embodiments and are identified with corresponding reference symbols in the respective drawing figures.

Each of the ring-shaped first thermocouple materials 38, 38' has a strip-shaped radial extension leading, respectively, to the terminal pads 43, 43'. Furthermore, there is a common terminal pad 44 arranged on the centerline that runs perpendicular to an imaginary connecting line between the respective center points 4, 4' of the measurement positions 3, 3'. Originating from the common terminal pad 44, a connecting lead 45 runs along the centerline between the two terminal pads 43, 43' to a Y-shaped juncture where the connecting lead 45 branches out into two strip-shaped arms 46, 46' which extend in mirror-symmetry relative to the centerline into the ring-shaped first thermocouple materials 38 and 38', respectively. The terminal pad 44, the connecting lead 45 and its arms 46, 46' consist of a second thermocouple material which forms thermocouple junctions at the connections to the first thermocouple materials 38 and 38'. The thermoelectric signals that occur at these two thermocouple junctions can be tapped between the common terminal pad 44 and the respective terminal pads 43 and 43'. The two thermoelectric signals correspond to the respective absolute temperatures at the measurement positions 3 and 3'. For the determination of the absolute temperature values, the signal is further processed in a known manner through an appropriate circuit arrangement.

In all embodiments of the foregoing description, the sensor is thermally coupled to a heat source through thermal contact between a border area of the substrate 1 and the heat source. This can be achieved, e.g., if a ring-shaped border area of the bottom side of the sensor, i.e., the reverse side of the top surface 2, is seated on an appropriately shaped heat-conducting flange of the heat source. Specifically, the ring-shaped border area can be delimited on the outside by the radially outer border of the cylindrical disk that forms the substrate 1 and on the inside by a cutback in the shape of a flat cylinder whose radius is somewhat smaller than the radius of the substrate 1.

The radial temperature gradients that occur relative to the center points 4, 4' of the measurement positions 3, 3', 30, 31, 32, 33 are the reason for the thermoelectric voltages that are generated between the thermocouple junctions 5 and 8 as well as between the junctions 9 and 10, which are radially distanced from each other. These temperature gradients increase with decreasing thermal conductivity of the substrate 1. Therefore, in order to achieve a high sensitivity of the sensor, substrates with a relatively small thermal conductivity λ can be used, specifically with λ not exceeding 5 W/(m·K), preferably with λ not exceeding 3 W/(m·K) or even not exceeding 2 W/(m·K). Substrates 1 that have been found suitable are ceramics with special properties, for example made of the ceramic material that is available under the trade name PYTHAGORAS, or made of the glass-ceramic material that is available under the trade name MACOR, which has a λ-value of about 1.5 W/(m·K).

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A thermoanalytical sensor comprising:
    a substrate;
    at least one measurement position;
    a thermocouple arrangement, which is formed on a substantially planar surface of the substrate to deliver a thermoelectric signal;
    wherein said substrate is constructed for thermal coupling to a heat source and can conduct a heat flow between said heat source and said measurement position;
    wherein said thermocouple arrangement comprises a serial chain of thermocouple junctions that is associated with said measurement position;
    wherein the thermocouple junctions are connected to each other in a circuit arrangement and wherein each thermocouple junction is composed of two different thermocouple materials;
    wherein said circuit arrangement comprises at least two partial patterns arranged in at least two planes, with at least one insulating layer separating the planes from each other;
    wherein each of the at least two partial patterns of the circuit arrangement comprise at least one interlayer contact, the interlayer contacts of the partial patterns connected to each other through interlayer contact holes formed in the at least one insulating layer; and
    wherein each partial pattern is connected to the next partial pattern by only one connection.

2. The thermoanalytical sensor according to claim 1, wherein the partial patterns that lie in different planes have substantially congruent shapes.

3. The thermoanalytical sensor according to claim 1, wherein at least one of the partial patterns comprises a plurality of first thermocouple junctions lying on a first circle whose midpoint is located at the center of the measurement position, a plurality of second thermocouple junctions lying on a second circle concentric to the first circle, a plurality of third thermocouple junctions lying on a third circle that is concentric to the first to circle, and a plurality of fourth thermocouple junctions lying on a fourth circle that is concentric to the first circle.

4. The thermoanalytical sensor according to claim 3, wherein the first circle comprises a first radius, the second circle comprises a second radius, the third circle comprises a third radius, and the fourth circle comprises a fourth radius, and wherein the second radius is larger than the first radius, the third radius is larger than the first radius and smaller than the second radius, and the fourth radius is larger than the second radius.

5. The thermoanalytical sensor according to claim 1, wherein at least one of the partial patterns comprise terminals for tapping the thermoelectric signal of the thermocouple arrangement.

6. The thermoanalytical sensor according to claim 5, wherein the thermocouple junctions of all of the partial patterns are connected in series.

7. The thermoanalytical sensor according to claim 6, wherein the thermocouple junctions are arranged so that they proceed in the azimuthal direction around the center of the measurement position and lie at alternatingly different radial distances from the center of the measurement position.

8. A method of manufacturing the thermoanalytical sensor of claim 1, the method comprising:

printing a pattern composed of at least two different thermocouple material pastes by way of a thick-film technique onto a substantially planar surface of the substrate, wherein the pattern represents the thermocouple arrangement comprising a serially connected chain of thermocouple junctions that is associated with the at least one measurement position operable to deliver a thermoelectric signal;

firing the pattern after printing, wherein the pattern is divided into at least two partial patterns, one of the partial patterns being produced on the substrate, said one of the partial patterns being overlaid with the insulating layer with interlayer contact holes for connection of the partial patterns, and a further one of the partial patterns being produced on the insulating layer;

each of the partial patterns is connected to a next partial pattern by only one connection; and repeating the printing and firing until all partial patterns have been produced.

9. The method according to claim 8, wherein the partial patterns have substantially congruent shapes.

10. The method according to claim 8, comprising:

producing an insulating layer with connector terminals on top of a topmost partial pattern relative to the substrate, wherein the thermoelectric signal can be tapped from said connector terminals, and wherein at least one of the connector terminals is joined through an interlayer contact to a partial pattern in a bottom layer relative to the substrate.

* * * * *